United States Patent [19]
Horn

[11] Patent Number: 5,363,040
[45] Date of Patent: Nov. 8, 1994

[54] NON-DESTRUCTIVE EDDY CURRENT PART TESTING USING THERMAL PRINTING

[76] Inventor: Michael Horn, 35 Lucille Dr. S., Setauket, N.Y. 11720

[21] Appl. No.: 21,466

[22] Filed: Feb. 23, 1993

[51] Int. Cl.⁵ .................. G01N 27/90; G01D 9/00; G01D 15/10
[52] U.S. Cl. ........................ 324/238; 33/666; 324/226; 324/262; 246/33 F
[58] Field of Search .......... 324/213, 216, 226, 237, 324/238, 240, 262; 33/666; 346/33 F

[56] References Cited

U.S. PATENT DOCUMENTS

| | | | |
|---|---|---|---|
| 1,971,189 | 8/1934 | Leibing | 324/67 |
| 2,129,058 | 9/1938 | Hedden | 324/329 X |
| 2,660,704 | 11/1953 | Harmon et al. | 324/237 |
| 3,611,121 | 10/1971 | Vild et al. | 324/238 |
| 4,365,198 | 12/1982 | Toth | 324/226 |
| 5,172,055 | 12/1992 | Horn | 324/262 X |

*Primary Examiner*—Gerard R. Strecker
*Attorney, Agent, or Firm*—Pollock Vande Sande & Priddy

[57] ABSTRACT

A scan head includes an eddy current probe and a thermal print head. A sheet of thermal paper is mounted to the top of a laminated part being inspected and the scan head is moved across the surface of the part. A map of defect markings will appear on the thermal paper in a 1-to-1 relationship with the actual sub-surface defects. This greatly expedites the inspection process since the mapped defects are in spatial correspondence with the actual part.

3 Claims, 1 Drawing Sheet

NON-DESTRUCTIVE EDDY CURRENT PART TESTING USING THERMAL PRINTING

FIELD OF THE INVENTION

The present invention relates to non-destructive testing of parts utilizing eddy current mapping of internal defects.

BACKGROUND OF THE INVENTION

The collection of data from test instruments, in particular nondestructive inspection (NDI) tests, are best presented as a map proportional to the areas tested or scanned. For example, eddy current scans of a laminated part surface are often made to determine subsurface corrosion. Typically, the recorded data is presented on a monitor and various techniques are employed to translate the location of a defect from an XY display onto the part itself. However, this is quite time consuming and prone to error.

Accordingly, it would be a great advantage to be able to map such data directly onto the part or onto a sheet which overlies the part, thereby presenting mapping of the data as a pictorial overview of the data in a form most easily interpreted by an inspector.

BRIEF DESCRIPTION OF THE PRESENT INVENTION

The present invention incorporates a conventional scanning or test probe such as the above-mentioned eddy current type. However, it should be emphasized that other types of conventional probes may be employed. Other types include harmonic and magnetic bond probe. The probe itself is mounted in close proximity with an automatic marking device within the housing of a scanning head. The marker is preferably a thermal print head but other types of electrically actuated marking devices may be employed.

The probe device inputs its signals to a computer which has a preset threshold for detection of sub-surface problems. When the scan head is moved over a problem area, the probe detection signal will exceed the preselected threshold and a mark will be made. In the case of using a thermal printer head, the surface being scanned is provided with a large sheet of thermal paper which is affixed to the part surface. Thus, when the thermal printer head is energized, a suitable mark is made on the thermal paper which is in registry with the problem area below the surface.

As the scan head is moved along the entire surface of the part, a map of defect areas becomes marked on a 1-to-1 relationship and in spatial correspondence to the actual part. This greatly facilitates the physical location of the problem areas for an inspector.

BRIEF DESCRIPTION OF THE FIGURES

The above-mentioned objects and advantages of the present invention will be more clearly understood when considered in conjunction with the accompanying drawings, in which.

DETAILED DESCRIPTION OF THE INVENTION

Figure 1:
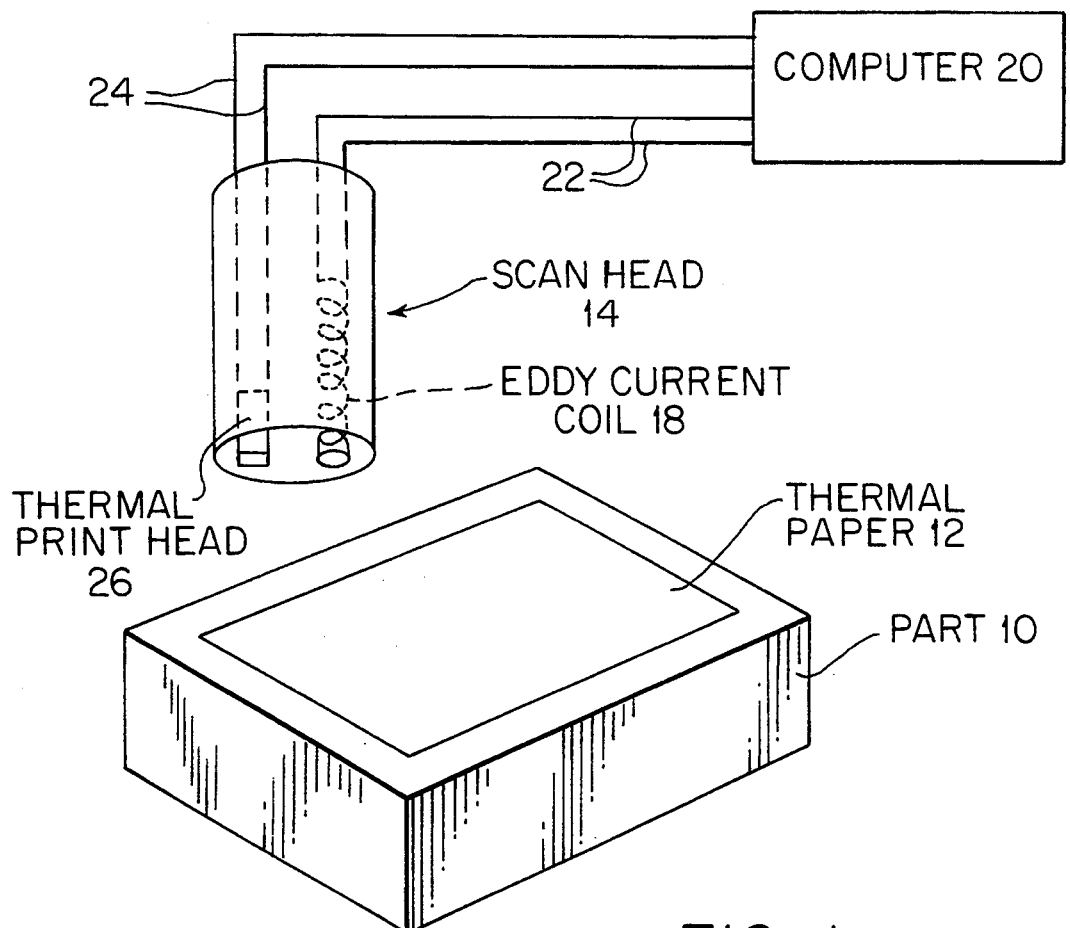
FIG. 1 is a perspective schematic view of the present invention when utilizing an eddy current coil as a probe and a thermal print head as a marking device.
Figure 2:
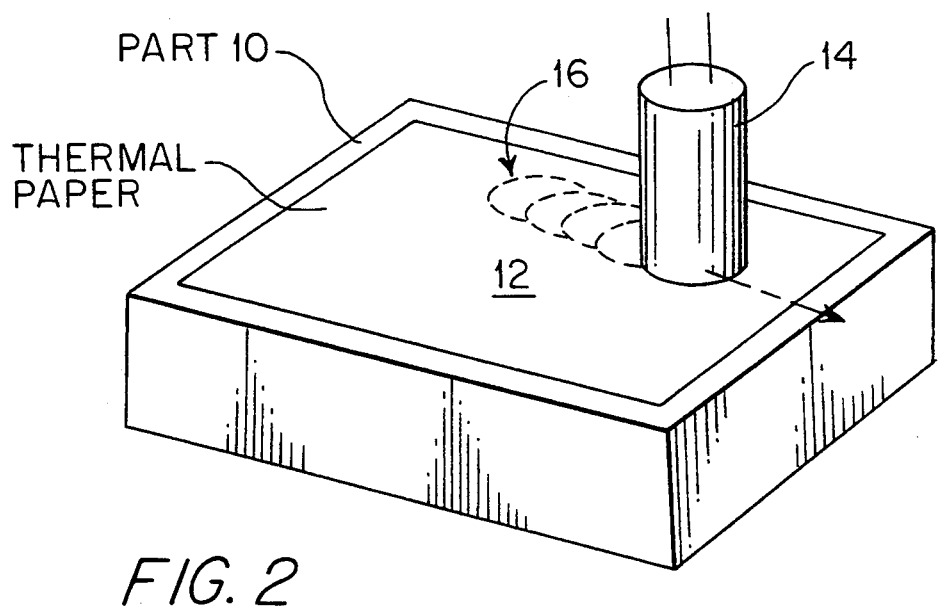
FIG. 2 indicates the scan head of the present invention building a map of defects as the head scans across the surface of a part being inspected.

FIGS. 1 and 2 illustrate the invention when utilizing the conventional eddy current coil as a probe and a conventional thermal print head as a marking device. Although this is a preferred embodiment of the invention, it is to be understood that other types of probes and marking devices may be employed as previously mentioned.

In FIG. 1 part 10 has a sheet of thermal paper 12 affixed to a surface thereof which will be directly scanned. A scan head 14 encloses a conventional eddy current coil 18 and thermal print head 26. These components are respectively connected via wires 22 and 24 to a computer 20 which performs a threshold detection function of the signals generated from the eddy current coil, and subsequent actuation of thermal print head 26 in those scanned areas where defects are detected.

FIG. 2 is a schematic illustration of the operation of the invention. As is indicated, the scan head 14 is moved across the face of the thermal paper 12 and marks 16 are generated in those areas where sub-surface defects are detected. When the scanning of the part has been completed, a map of all detected sub-surface defects has been marked on the thermal paper 12 and this gives an inspector a 1-to-1 indication as to where the effects occur in spatial correspondence to the actual part.

It should be understood that the invention is not limited to the exact details of construction shown and described herein for obvious modifications will occur to persons skilled in the art.

I claim:

1. An apparatus for mapping sub-surface defects in a part being inspected, comprising:
   a housing to scan a surface of the part;
   a probe for detecting sub-surface defects enclosed within the housing;
   a threshold detector for detecting an output of the probe which exceeds a predetermined level;
   a thermal print head enclosed within the housing, adjacent the probe, and connected to an output of the threshold detector for creating a mark signal when a sub-surface defect is detected; and
   thermal paper mounted on the surface to be scanned, permanent marks created on the paper by head, immediately upon occurrence of a mark signal, on a one-to-one size basis with all defects;
   wherein a permanently recorded map of defects is produced on the paper at the conclusion of a scanning operation.

2. The apparatus set forth in claim 1, wherein the probe of the apparatus is an eddy current coil.

3. A method for mapping sub-surface defects in a part being inspected, comprising the steps:
   mounting thermal paper to a surface of the part;
   scanning the surface of a part being inspected while electromagnetically probing the part;
   generating mark signals whenever a sub-surface defect, over a preselected threshold, is encountered during scanning;
   subjecting a scanned point on the paper to heat, in immediate response to a generated mark signal, thus creating a permanently recorded mark on the paper, immediately adjacent a point being probed when a mark signal is generated; and
   developing a map of created marks at the conclusion of a scanning operation, the map spatially corresponding with the detected sub-surface defects on a one-to-one basis.

* * * * *